United States Patent [19]
Mueninghoff et al.

[11] Patent Number: 6,057,267
[45] Date of Patent: May 2, 2000

[54] USE OF FATTY ALCOHOL CARBONATES AS SOLVENTS IN AGRICULTURAL FORMULATIONS

[75] Inventors: Jane C. Mueninghoff, The Woodlands, Tex.; Roger H. Garst, Cincinnati, Ohio

[73] Assignee: Henkel Corporation, Gulph Mills, Pa.

[21] Appl. No.: 09/197,803

[22] Filed: Nov. 23, 1998

Related U.S. Application Data

[60] Provisional application No. 60/067,611, Dec. 5, 1997.

[51] Int. Cl.$^7$ ..................................................... A01N 25/30
[52] U.S. Cl. ........................... 504/116; 424/405; 514/975
[58] Field of Search ............................ 504/116; 424/405; 514/975; 516/204

[56] References Cited

U.S. PATENT DOCUMENTS

| | | | |
|---|---|---|---|
| 3,723,444 | 3/1973 | Colchester et al. | 260/295 AM |
| 4,159,943 | 7/1979 | Petrovich | 209/166 |
| 4,390,463 | 6/1983 | Boden et al. | 252/522 R |
| 5,258,541 | 11/1993 | Yokota et al. | 558/260 |
| 5,348,712 | 9/1994 | Marquis et al. | 423/22 |
| 5,635,441 | 6/1997 | Sam et al. | 503/227 |

OTHER PUBLICATIONS

Kirk–Othmer Encyclopedia of Chemical Technology, 4th ed., New York, 1993, vol. 5, pp. 77, 87–97.

*Primary Examiner*—S. Mark Clardy
*Attorney, Agent, or Firm*—John E. Drach; Steven J. Trzaska

[57] ABSTRACT

An adjuvant containing: (a) a fatty alcohol carbonate; and (b) a component selected from the group consisting of nonionic surfactants, anionic surfactants, cationic surfactants, alkyl esters, phytobland mineral oils, water soluble silicone surfactants, fatty acid dialkyl ethers, fatty acid dialkyl carbonates, vegetable oils, and mixtures thereof.

10 Claims, No Drawings

USE OF FATTY ALCOHOL CARBONATES AS SOLVENTS IN AGRICULTURAL FORMULATIONS

CROSS-REFERENCE TO RELATED APPLICATION

This application claims the benefit of earlier filed and copending provisional application Ser. No. 60/067,611, filed on Dec. 5, 1997, the entire contents of which are incorporated herein by reference.

STATEMENT REGARDING FEDERALLY SPONSORED RESEARCH OR DEVELOPMENT

Not Applicable.

BACKGROUND OF THE INVENTION

The present invention generally relates to solvents for agricultural products. More particularly, the invention relates to the use of methyl ester invert solvents for the formulation of pesticide products.

It is known that various agricultural products such as insecticides, insect repellents, fungicides, bactericides, herbicides, and plant growth regulators may be formulated into various pesticide products for use on crops and ornamental plants, for controlling weeds, insects and the like. These products may be applied in the form of a liquid or a semi-solid dispersion.

While the use and application of pesticide formulations is generally known, their formulation into a single, yet compatibly soluble pesticide product poses various solubility problems. Due to the chemical dissimilarities associated with the individual components which make up a pesticide formulation, it is oftentimes not possible to effectively disperse the pesticide component into a single, uniform, formulation.

BRIEF SUMMARY OF THE INVENTION

The present invention is directed to an adjuvant composition containing:

(a) a fatty alcohol carbonate; and
(b) a component selected from the group consisting of nonionic surfactants, anionic surfactants, cationic surfactants, alkyl esters, phytobland mineral oils, water soluble silicone surfactants, fatty dialkyl ethers, fatty dialkyl carbonates, vegetable oils, and mixtures thereof.

The present invention is also directed to a pesticide concentrate containing:

(a) an adjuvant composition containing:
  (i) a fatty alcohol carbonate; and
  (ii) a component selected from the group consisting of nonionic surfactants, anionic surfactants, cationic surfactants, alkyl esters, phytobland mineral oils, water soluble silicone surfactants, fatty dialkyl ethers, fatty dialkyl carbonates, vegetable oils, and mixtures thereof; and
(b) a biologically-active ingredient.

The present invention is also directed to a process for treating a target substrate involving contacting the target substrate with the above-disclosed pesticide concentrate.

BRIEF DESCRIPTION OF THE SEVERAL VIEWS OF THE DRAWING

Not Applicable.

DETAILED DESCRIPTION OF THE INVENTION

Other than in the claims and in the operating examples, or where otherwise indicated, all numbers expressing quantities of ingredients or reaction conditions used herein are to be understood as being modified in all instances by the term "about".

The term target substrate as used herein means a plant, a plant pest, or a combination of a plant and a plant pest. A plant pest is defined as any living stage of any weed, insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The fatty alcohol carbonates of the present invention can be used either alone, or in combination, with other known solvents such as, for example, fatty acid methyl esters. They can be used as solvents in pesticide formulations such as emulsifiable concentrates and concentrated emulsions.

These fatty alcohol carbonates are naturally derived, biodegradable materials which can be used as solvents in combination with a variety of active ingredients because of their inherent polarity. These compounds are hydrolytically stable which is very important when employing agricultural tank mixes.

Suitable fatty alcohol carbonates which may be employed in the present invention correspond to formula I:

$$R_1\text{—}O\text{—}CO\text{—}O\text{—}R_1 \qquad (I)$$

wherein $R_1$ is a $C_{6-22}$ aliphatic hydrocarbyl, and preferably a $C_{12-18}$ aliphatic hydrocarbyl, having from 0 to 3 double bonds. These compounds are prepared by transesterifying diethyl carbonate.

Examples of suitable co-surfactants/solvents include, for example, other nonionic surfactants such as ethoxylated castor oils, alcohol ethoxylates, alkyl polyglycosides, glucamides and the like, anionic surfactants such as fatty alcohol ether sulfates, phosphate esters, sulfonates, and the like, cationic surfactants such as ethoxylated fatty amines, and the like, alkyl esters such as methyl oleate, ethyl canolate, and methyl soyate, phytobland mineral oils, water-soluble silicone surfactants, fatty dialkyl ethers, fatty dialkyl carbonates, vegetable oils such as canola oil, soybean oil and the like, and mixtures thereof, typically employed in adjuvant and pesticide compositions.

According to one embodiment of the present invention, there is provided an adjuvant composition containing: (a) from about 99 to about 1% by weight, preferably from about 90 to about 10% by weight, and most preferably from about 75 to about 25% by weight of a fatty alcohol carbonate, and (b) from about 1 to about 99% by weight, preferably from about 10 to about 90% by weight, and most preferably from about 25 to about 75% by weight, based on the weight of the adjuvant composition, of a co-surfactant/solvent.

According to another embodiment of the present invention, there is provided a pesticide concentrate containing a mixture of the above-disclosed adjuvant composition and a biologically active ingredient.

Suitable biologically-active ingredients for use in the pesticide concentrates of the present invention are generally selected from the group consisting of insecticides, insect repellents, fungicides, bactericides, bacteriostats, herbicides, and plant growth regulators, all of which are based on biologically-active ingredients. Suitable insecticides include, for example,
O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl) phosphorodithioate, O,O-dimethyl S-2-[(ethylthio)ethyl]phosphorodithioate, O,O-diethyl S-2-[(ethylthio)ethyl]phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl) thiophosphate, O-ethyl O-p-cyanophenyl-O-phenylphosphorothioate, O,O-dimethyl-S-(1,2-dicarboethoxyethyl) phosphorodithioate, 2-chloro-(2,4,5-trichlorophenyl)vinyidimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate O,O-diethyl O-(3-oxo-2-phenyl-2H-pyridazine-6-yl)phosphorothioate, O,O-dimethyl S-(1-methyl-2-ethylsulfinyl)-ethyl phosphorothioate, O,O-dimethyl S-phthalimidomethyl phosphorodithioate, O,O-diethyl 2,2,2-trichloroethanol, 2-(p-tert-butyl-phenoxy)isopropyl-2'-chloroethylsulfite, azoxybenzene, di-(p-chlorophenyl)cyclopropyl carbinol, di[tri(2,2-dimethyl-2-phenylethyl)tin]oxide, 1-(4-chlorophenyl)-3-(2,6-difluorobenzoyl)urea and S-tricyclohexyltin O,O-diisopropylphosphorodithioate; 2-methyl-2-(methylthio)propionaldehyde O-(methylcarbamoyl)oxime; ethyl [2-(4-phenoxyphenoxy) ethyl] carbamate; butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4-phenoxybutyl)dimethylthiocarbamate; dimethyl N,N'-(thiobis(methylimino)carbonyloxy)-bis (ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2,2-dichloro-1-(4-ethoxyphenyl)cyclopropanecarboxylate; (RS)-α-cyano-3-phenoxybenzyl-N-(2-chloro-α,α,α-trifluoro-p-tolyl-D-valinate;
3-phenoxybenzyl-(1RS)-cis,trans-3-(2,2-dichlorovinyl)-2,2-dimethylcyclopropanedicarboxylate.

Insect repellents which may be employed include but are not limited to 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may be employed include but are not limited to 3,3'-ethylenebis (tetrahydro-4,6-dimethyl-2H-1,3,5-thiadiazine-2-thione), zinc or manganese ethylenebis (dithiocarbamate), bis-(dimethyldithiocarbamoyl) disulfide, zinc propylenebis (dithiocarbamate), bis (dimethyldithiocarbamoyl) ethylenediamine; nickel dimethyidithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10, 11-dehydrodibenzo (b,f)azepine; pyridine fungicides such as zinc bis(1-hydroxy-2(1H) pyridinethionate and 2-pyridinethiol-1-oxide sodium salt; O,O-diisopropyl S-benzylphosphorothioate and O-ethyl S,S-diphenyidithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio 4-cyclohexene-1,2-dicarboxyimide and N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate, pentachloronitrobenzene; 1,4-dichloro-2,5-dimethoxybenzene; 5-methyl-s-triazol-(3,4b)benzthiazole; 2-(thiocyanomethylthio)benzothiazole; 3-hydroxy-5-methylisooxazole; N-2,3-dichlorophenyltetrachlorophthatamic acid; 5-ethoxy-3-trichloromethyl-1,2,4-thiaziazole; 2,4-dichloro-6-(O-chloroanilino)-1,3,5-triazine; 2,3-dicyano-1,4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)5-ethenyl 5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyidithiocarbonylimidate; 4-chlorophenoxy-3,3-dimethyl-1-(1H,1,3,4-triazol-1-yl)-2-butanone; methyl-D, L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolol-[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethylaminopropyl) thiocarbamate hydrochloride; piomycin; S,S-6-methylquinoxaline-2,3-di-yldithiocarbonate; complex of zinc and manneb; di-zinc bis(dimethyidithiocarbamate) ethylenebis (dithiocarbamate).

Plant growth regulators which may be employed include but are not limited to N-methoxycaronyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4, 6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof.

2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether,2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate,S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-dimethyl-4,4'-bispyridinium dichloride; phosphoric herbicides such as N-(phosphonomethyl)glycine; aniline herbicides such as alpha-trifluoro-2,6-dinitro-N,N-dipropyl-p-toluidine, 4-(methylsulfonyl)-2,6-dinitro-N,N-dipropylaniline and N[3], N[3]-diethyl-2,4-dinitro-6-trifluoromethyl-1,3-phenylene diamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl,N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methyl-phenoxy) pyridazine.

According to another embodiment of the present invention, there is thus provided a pesticide concentrate containing: (a) from about 99.9 to about 5% by weight, preferably from about 95 to about 15% by weight, and most preferably from about 90 to about 20% by weight, of the above-disclosed adjuvant; and (b) from about 0.1 to about 95% by weight, preferably from about 5 to about 85% by weight, and most preferably from about 10 to about 80% by weight, of a biologically active ingredient.

The precise amount of biologically active ingredient contained in the pesticide concentrate will oftentimes depend upon the specific end-use application, i.e., the target substrate to be treated, the area to be treated, etc. Thus, it is within the skill of the applicator to determine the specific amount of biologically active ingredient to be used for a particular application.

In order to formulate the pesticide concentrate into a ready-to-use form, it is typically diluted with water to form an aqueous pesticide composition. The ready-to-use aqueous pesticide composition will typically contain from about 0.1% to about 10% by weight, and preferably from about 0.5 to about 5% by weight, based on the weight of the composition, of the above-disclosed pesticide concentrate, the remainder of which will typically be water.

The precise amount of dilution of the pesticide concentrate necessary to form a ready-to-use aqueous pesticide composition will again depend upon the specific application itself, i.e., the target substrate to be treated, the area to be treated, etc. Thus, it is once again within the skill of the applicator to determine the specific amount of water needed to dilute the pesticide concentrate.

Finally, the present invention also provides for a process for treating a target substrate involving contacting the target substrate with the above-disclosed aqueous pesticide composition.

What is claimed is:

1. A pesticide concentrate comprising:
   (a) an adjuvant containing:
      (i) a fatty alcohol carbonate; and
      (ii) a component selected from the group consisting of nonionic surfactants, anionic surfactants, cationic surfactants, alkyl esters, phytobland mineral oils, water soluble silicone surfactants, fatty acid dialkyl ethers, fatty acid dialkyl carbonates, vegetable oils, and mixtures thereof; and
   (b) a biologically active ingredient.

2. The concentrate of claim 1 wherein the fatty alcohol carbonate is present in the adjuvant in an amount of from about 99 to about 1% by weight, based on the weight of the adjuvant.

3. The concentrate of claim 1 wherein the fatty alcohol carbonate is present in the adjuvant in an amount of from about 75 to about 25% by weight, based on the weight of the adjuvant.

4. The concentrate of claim 1 wherein the co-surfactant/solvent is present in the adjuvant in an amount of from about 1 to about 99% by weight, based on the weight of the adjuvant.

5. The concentrate of claim 1 wherein the co-surfactant/solvent is present in the adjuvant in an amount of from about 25 to about 75% by weight, based on the weight of the adjuvant.

6. The concentrate of claim 1 wherein the adjuvant is present in the concentrate in an amount of from about 99.9 to about 5% by weight, based on the weight of the concentrate.

7. The concentrate of claim 1 wherein the adjuvant is present in the concentrate in an amount of from about 90 to about 20% by weight, based on the weight of the concentrate.

8. The concentrate of claim 1 wherein the biologically active ingredient is present in the concentrate in an amount of from about 0.1 to about 95% by weight, based on the weight of the concentrate.

9. The concentrate of claim 1 wherein the biologically active ingredient is present in the concentrate in an amount of from about 10 to about 80% by weight, based on the weight of the concentrate.

10. A process for treating a target substrate comprising contacting the substrate with an effective amount of the pesticide concentrate of claim 1.

* * * * *